(12) United States Patent
Self et al.

(10) Patent No.: US 11,360,965 B1
(45) Date of Patent: Jun. 14, 2022

(54) METHOD, APPARATUS, AND COMPUTER PROGRAM PRODUCT FOR DYNAMICALLY UPDATING DATABASE TABLES

(71) Applicant: HealthStream, Inc., Nashville, TN (US)

(72) Inventors: Bryan Self, Birmingham, AL (US); Shawn Brezny, Lino Lakes, MN (US); Timothy Gruber, Helena, AL (US); John Graham, Birmingham, AL (US); Jnani Clay, Indianapolis, IN (US)

(73) Assignee: HealthStream, Inc., Nashville, TN (US)

( * ) Notice: Subject to any disclaimer, the term of this patent is extended or adjusted under 35 U.S.C. 154(b) by 254 days.

(21) Appl. No.: 16/741,403

(22) Filed: Jan. 13, 2020

(51) Int. Cl.
*G06F 16/20* (2019.01)
*G06F 16/23* (2019.01)
*G06F 16/22* (2019.01)
*G06F 21/62* (2013.01)
*G06F 16/93* (2019.01)

(52) U.S. Cl.
CPC ...... *G06F 16/2379* (2019.01); *G06F 16/2282* (2019.01); *G06F 16/2291* (2019.01); *G06F 16/93* (2019.01); *G06F 21/6218* (2013.01)

(58) Field of Classification Search
CPC .. G06F 16/2379; G06F 16/93; G06F 16/2281; G06F 16/2282; G06F 16/2291; G06F 16/6218
See application file for complete search history.

(56) References Cited

U.S. PATENT DOCUMENTS

| | | | |
|---|---|---|---|
| 8,949,781 B1* | 2/2015 | Orcutt | G06F 8/20 717/109 |
| 9,268,763 B1* | 2/2016 | Esho | G06F 16/93 |
| 2007/0079282 A1* | 4/2007 | Nachnani | G06F 8/34 717/106 |
| 2008/0304632 A1* | 12/2008 | Catlin | H04M 3/4938 379/88.04 |
| 2009/0125387 A1* | 5/2009 | Mak | G06Q 30/0277 705/14.73 |
| 2013/0132106 A1* | 5/2013 | Perry | G06Q 10/10 705/2 |
| 2013/0311516 A1* | 11/2013 | Callans | G16H 40/20 707/798 |
| 2014/0032485 A1* | 1/2014 | Perelman | G06F 40/174 707/608 |
| 2015/0213406 A1* | 7/2015 | Markham | G06Q 10/10 705/342 |
| 2016/0070758 A1* | 3/2016 | Thomson | G16H 10/60 707/781 |
| 2016/0253467 A1* | 9/2016 | Kitagawa | G16H 50/20 705/2 |

* cited by examiner

*Primary Examiner* — Tarek Chbouki
(74) *Attorney, Agent, or Firm* — A. J. Bahou; Chris McNeill; Waller Lansden Dortch & Davis LLP

(57) ABSTRACT

A method, apparatus, and computer program product are provided for dynamically updating database tables by generating dynamic field tracking forms. The method retrieves, based on an application bundle, values associated with a plurality of fields from a database, and dynamically generates and transmits a structured document and associated script based on the retrieved values. The method further receives an indication of a custom field, stores the custom field and associated values, and dynamically re-generates and re-transmits an updated structured document to allow for real-time or near real-time customization and database storage.

18 Claims, 6 Drawing Sheets

```xml
<!-- APPLICATION BUNDLE_A FIELDS -->
<CUSTOMFIELD IDENT="OTN" DESC="OT NUMBER" FIELD="OT" ENTITYTYPE="PATIENT" APPLICATION="BUNDLE_A"/>
<CUSTOMFIELD IDENT="PREHABDATE" DESC="PREHAB DATE" FIELD="PREHABDATE" WIDGETTYPE="2" ENTITYTYPE="PATIENT" APPLICATION="BUNDLE_A"/>
<CUSTOMFIELD IDENT="PREOPDATE" DESC="PRE-OP DATE" FIELD="PREHABDATE" WIDGETTYPE="2" ENTITYTYPE="PATIENT" APPLICATION="BUNDLE_A"/>
<CUSTOMFIELD IDENT="SUGERYDATE" DESC="SURGERY DATE" FIELD="SUGERYDATE" WIDGETTYPE="2" ENTITYTYPE="PATIENT" APPLICATION="BUNDLE_A"/>
<CUSTOMFIELD IDENT="PREFRLOC" DESC="PREF RHB LOC" FIELD="PREFRLOC" WIDGETTYPE="1" ENTITYTYPE="PATIENT" APPLICATION="BUNDLE_A"/>
<CUSTOMFIELD IDENT="BTODIS" DESC="BARRIER TO DSCG" FIELD="BTODIS" WIDGETTYPE="0" ENTITYTYPE="PATIENT" APPLICATION="BUNDLE_A"/>
<CUSTOMFIELD IDENT="CRND2CD" DESC="CRND 2 CALL DATE" FIELD="CRND2CD" WIDGETTYPE="2" ENTITYTYPE="PATIENT" APPLICATION="BUNDLE_A"/>
<CUSTOMFIELD IDENT="PIC" DESC="PT INIT CALL" FIELD="PIC" WIDGETTYPE="2" ENTITYTYPE="PATIENT" APPLICATION="BUNDLE_A"/>
<CUSTOMFIELD IDENT="NACRS" DESC="NACRS TRACKED" FIELD="NACRS" WIDGETTYPE="0" ENTITYTYPE="PATIENT" APPLICATION="BUNDLE_A"/>
```

METHOD, APPARATUS, AND COMPUTER PROGRAM PRODUCT FOR DYNAMICALLY UPDATING DATABASE TABLES

TECHNOLOGICAL FIELD

Embodiments of the present invention relate generally to computer technology and, more particularly, to methods, apparatuses, and computer program products for dynamically updating database tables by generating dynamic field tracking forms.

BACKGROUND

In a healthcare system, a variety of data may be collected on a particular patient throughout the course of the patient's visit to a particular healthcare facility. For example, various data may be observed during different stages, such as during a preadmission stage, an inpatient stage, and/or a discharge stage. Some data may relate to demographic data, medical data, insurance information, and/or the like, and may be entered and viewed via an electronic recordkeeping system or the like.

However, some computer applications may not enable access to or tracking of data desired to be tracked by healthcare practitioners (e.g., nurses, doctors, and medical staff). For instance, a healthcare practitioner may have to issue a specific request to a service provider to access certain data not available to the healthcare practitioner, or to begin tracking new or custom data fields within the existing system. The service provider may need to engage computer program developers and/or system administrators to make such changes to the computer application on the server and/or database in order to provide the relevant data to the healthcare practitioner and to enable tracking of new fields. The healthcare practitioner or other requestor may then incur wait time while the development changes are made, and servers may need to be rebooted to facilitate such changes to the applications.

BRIEF SUMMARY

Methods, apparatuses, and computer program products are therefore provided for dynamically updating database tables by generating dynamic field tracking forms. In one aspect, a method is provided comprising receiving at a server, from a client device during a client-server session, a request for data associated with at least one record and an application identifier. The method further comprises processing an application form associated with the application identifier to: (a) retrieve, from a database table, values associated with a plurality of fields associated with the application identifier and the at least one record, and (b) generate a structured document comprising the plurality of fields and the retrieved respective values. The method also comprises embedding, in the structured document, a script enabling customization of the structured document. The method further comprises transmitting the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server. The method also comprises receiving, at the server, the indication of the at least one custom field and the values of the at least one custom field. The method further comprises, during the client-server session, adding the at least one custom field to the database table and storing the values of the at least one custom field.

In some embodiments of the method, processing the application form further comprises accessing an application bundle comprising XML defining the plurality of fields associated with the application identifier, and the method further comprises, during the client-server session, modifying the application bundle or generating a new application bundle comprising XML and reflecting the at least one custom field. In some embodiments of the method, the database table to which the at least one custom field is added is in a first region, and the method further comprises exporting the application bundle to at least a second region to cause the at least one custom field to be added to at least a second database table of the second region. In some embodiments of the method, the script is further configured to, when executed by the client device, receive an indication of at least one respective widget type to be associated with the at least one custom field. In some embodiments of the method, the at least one record is associated with at least one patient identifier. In some embodiments of the method, processing the application form, embedding the script, and transmitting the structured document are performed in real-time or near real-time. In some embodiments of the method, the request comprises a role identifier, and the method further comprises determining whether a user associated with the role identifier is authorized to access the plurality of fields and, in an instance in which the user is not authorized to access the plurality of fields, transmitting an indication of a denial of the request to the client device. In some embodiments of the method, the script comprises one or more ECMAScript commands. In some embodiments of the method, the structured document is a Scalable Vector Graphics (SVG) document. In some embodiments of the method, the structured document is dynamically generated using JavaServer Pages (JSP). In some embodiments of the method, the displayed structured document is updated in real-time or near real-time to reflect the at least one custom field and the respective entered values. In some embodiments, the method further comprises receiving a file from a Health Level 7 (HL7) server and auto-populating data from the file into the database table.

An apparatus is also provided, comprising at least one processor and at least one memory including computer program code, the at least one memory and the computer program code configured to, with the processor, cause the apparatus to at least receive, from a client device during a client-server session, a request for data associated with at least one record and an application identifier. The apparatus is further configured, with the at least one memory and the computer program code, to process an application form associated with the application identifier to: (a) retrieve, from a database table, values associated with a plurality of fields associated with the application identifier and the at least one record, and (b) generate a structured document comprising the plurality of fields and the retrieved respective values. The apparatus is further configured, with the at least one memory and the computer program code, to embed in the structured document, a script enabling customization of the structured document. The apparatus is further configured, with the at least one memory and the computer program code, to transmit the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server. The apparatus is further configured, with the at least one memory and the computer program code, to receive, at the server, the indication of the at least one custom field and the values of the at least one custom field. The apparatus is further configured, with the at least one memory and the computer program code, to during the client-server session, adding the at least one custom field to the database table and storing the values of the at least one custom field.

In some embodiments of the apparatus, processing the application form further comprises accessing an application bundle comprising XML defining the plurality of fields associated with the application identifier, and the at least one memory and the computer program code are further configured to, with the processor, cause the apparatus to, during the client-server session, modify the application bundle or generate a new application bundle comprising XML and reflecting the at least one custom field. In some embodiments of the apparatus, the database table to which the at least one custom field is added is in a first region, and the at least one memory and the computer program code are further configured to, with the processor, cause the apparatus to export the application bundle to at least a second region to cause the at least one custom field to be added to at least a second database table of the second region. In some embodiments of the apparatus, the script is further configured to, when executed by the client device, receive an indication of at least one respective widget type to be associated with the at least one custom field. In some embodiments of the apparatus, the at least one record is associated with at least one patient identifier. In some embodiments of the apparatus, processing the application form, embedding the script, and transmitting the structured document are performed in real-time or near real-time. In some embodiments of the apparatus, the request comprises a role identifier, and the at least one memory and the computer program code are further configured to, with the processor, cause the apparatus to at least determine whether a user associated with the role identifier is authorized to access the plurality of fields and, in an instance in which the user is not authorized to access the plurality of fields, transmit an indication of a denial of the request to the client device. In some embodiments of the apparatus, the script comprises one or more ECMAScript commands. In some embodiments of the apparatus, the structured document is a Scalable Vector Graphics (SVG) document. In some embodiments of the apparatus, the structured document is dynamically generated using Java-Server Pages (JSP). In some embodiments of the apparatus, the displayed structured document is updated in real-time or near real-time to reflect the at least one custom field and the respective entered values. In some embodiments, the apparatus is further configured to receive a file from a Health Level 7 (HL7) server and auto-populating data from the file into the database table.

A computer program product is also provided, the computer program product comprising at least one non-transitory computer-readable storage medium having computer-executable program code instructions stored therein, the computer-executable program code instructions comprising program code instructions to receive, from a client device during a client-server session, a request for data associated with at least one record and an application identifier. The program code instructions are further configured to process an application form associated with the application identifier to: (a) retrieve, from a database table, values associated with a plurality of fields associated with the application identifier and the at least one record, and (b) generate a structured document comprising the plurality of fields and the retrieved respective values. The program code instructions are further configured to embed, in the structured document, a script enabling customization of the structured document. The program code instructions are further configured to transmit the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server. The program code instructions are further configured to receive, at the server, the indication of the at least one custom field and the values of the at least one custom field. The program code instructions are further configured to, during the client-server session, adding the at least one custom field to the database table and storing the values of the at least one custom field.

In some embodiments of the computer program product, processing the application form further comprises accessing an application bundle comprising XML defining the plurality of fields associated with the application identifier, and the program code instructions are further configured to, during the client-server session, modify the application bundle or generate a new application bundle comprising XML and reflecting the at least one custom field. In some embodiments of the computer program product, the database table to which the at least one custom field is added is in a first region, and program code instructions are further configured to export the application bundle to at least a second region to cause the at least one custom field to be added to at least a second database table of the second region. In some embodiments of the computer program product, the script is further configured to, when executed by the client device, receive an indication of at least one respective widget type to be associated with the at least one custom field. In some embodiments of the computer program product, the at least one record is associated with at least one patient identifier. In some embodiments of the computer program product, processing the application form, embedding the script, and transmitting the structured document are performed in real-time or near real-time. In some embodiments of the computer program product, the request comprises a role identifier, and the program code instructions are further configured to determine whether a user associated with the role identifier is authorized to access the plurality of fields and, in an instance in which the user is not authorized to access the plurality of fields, transmit an indication of a denial of the request to the client device. In some embodiments of the computer program product, the script comprises one or more ECMAScript commands. In some embodiments of the computer program product, the structured document is a Scalable Vector Graphics (SVG) document. In some embodiments of the computer program product, the structured document is dynamically generated using JavaServer Pages (JSP). In some embodiments of the computer program product, the displayed structured document is updated in real-time or near real-time to reflect the at least one custom field and the respective entered values. In some embodiments, the program code instructions are further configured to receive a file from a Health Level 7 (HL7) server and auto-populating data from the file into the database table.

An apparatus is provided with means for receiving at a server, from a client device during a client-server session, a request for data associated with at least one record and an application identifier. The apparatus further comprises means for processing an application form associated with the application identifier to: (a) retrieve, from a database table, values associated with a plurality of fields associated with the application identifier and the at least one record, and (b) generate a structured document comprising the plurality of fields and the retrieved respective values. The apparatus also comprises means for embedding, in the structured document, a script enabling customization of the structured document. The apparatus further comprises means for transmitting the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server. The apparatus also includes means for receiving, at the server, the indication of the at least one custom field and the values of the at least one custom field. The apparatus also includes means for, during the client-server session, adding the at least one custom field to the database table and storing the values of the at least one custom field.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
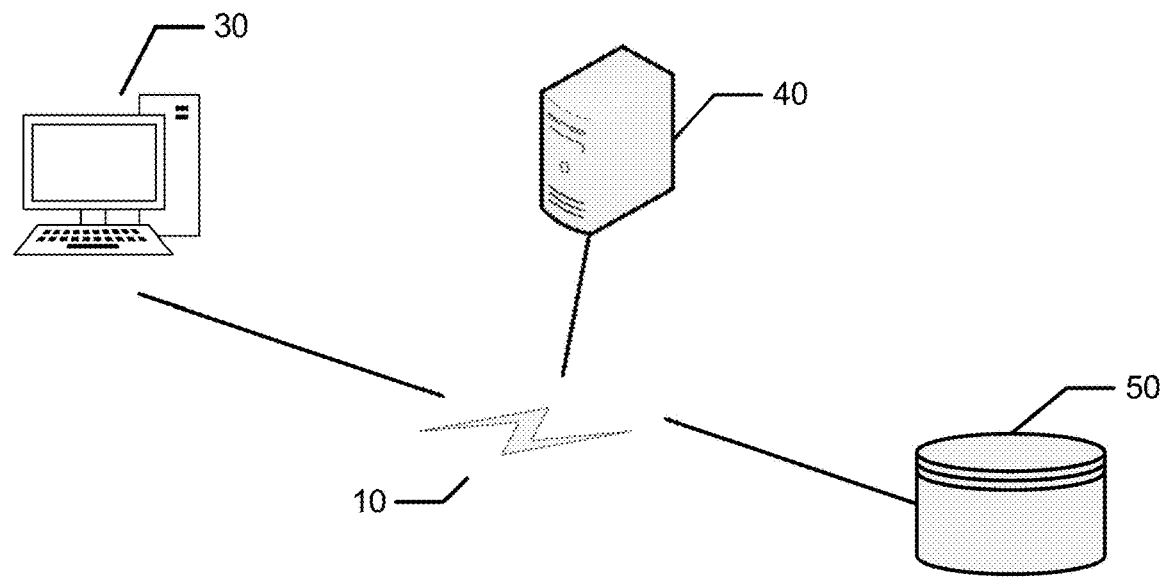
Figure 2:
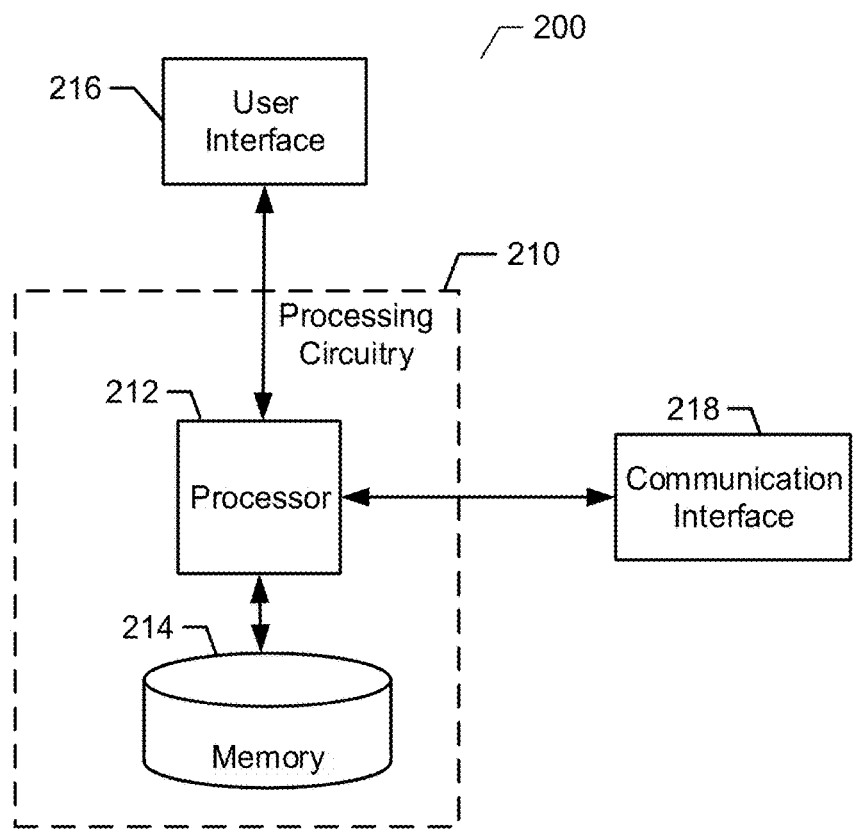
Figure 3:
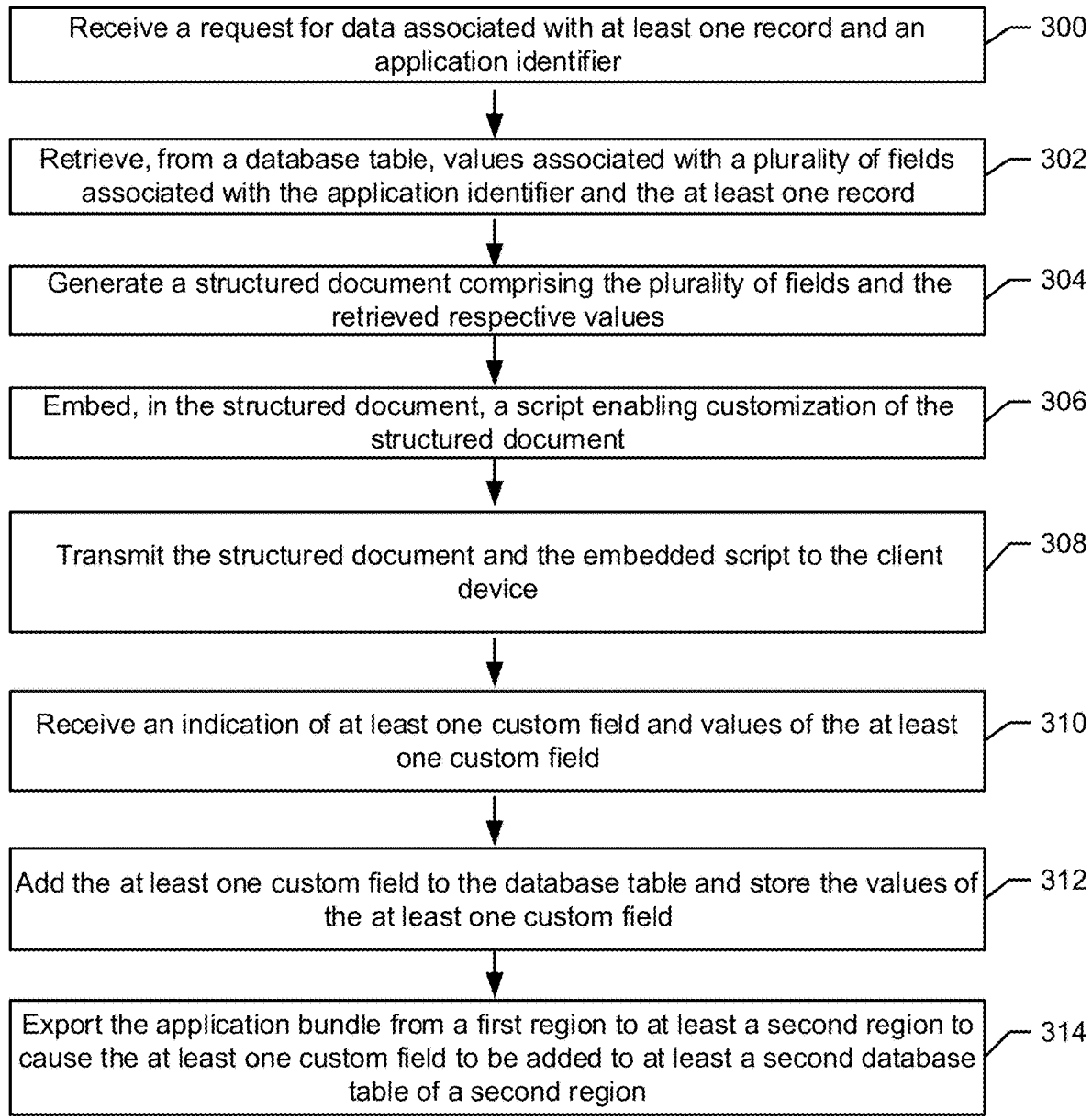
Figure 5A:
Figure 5B:
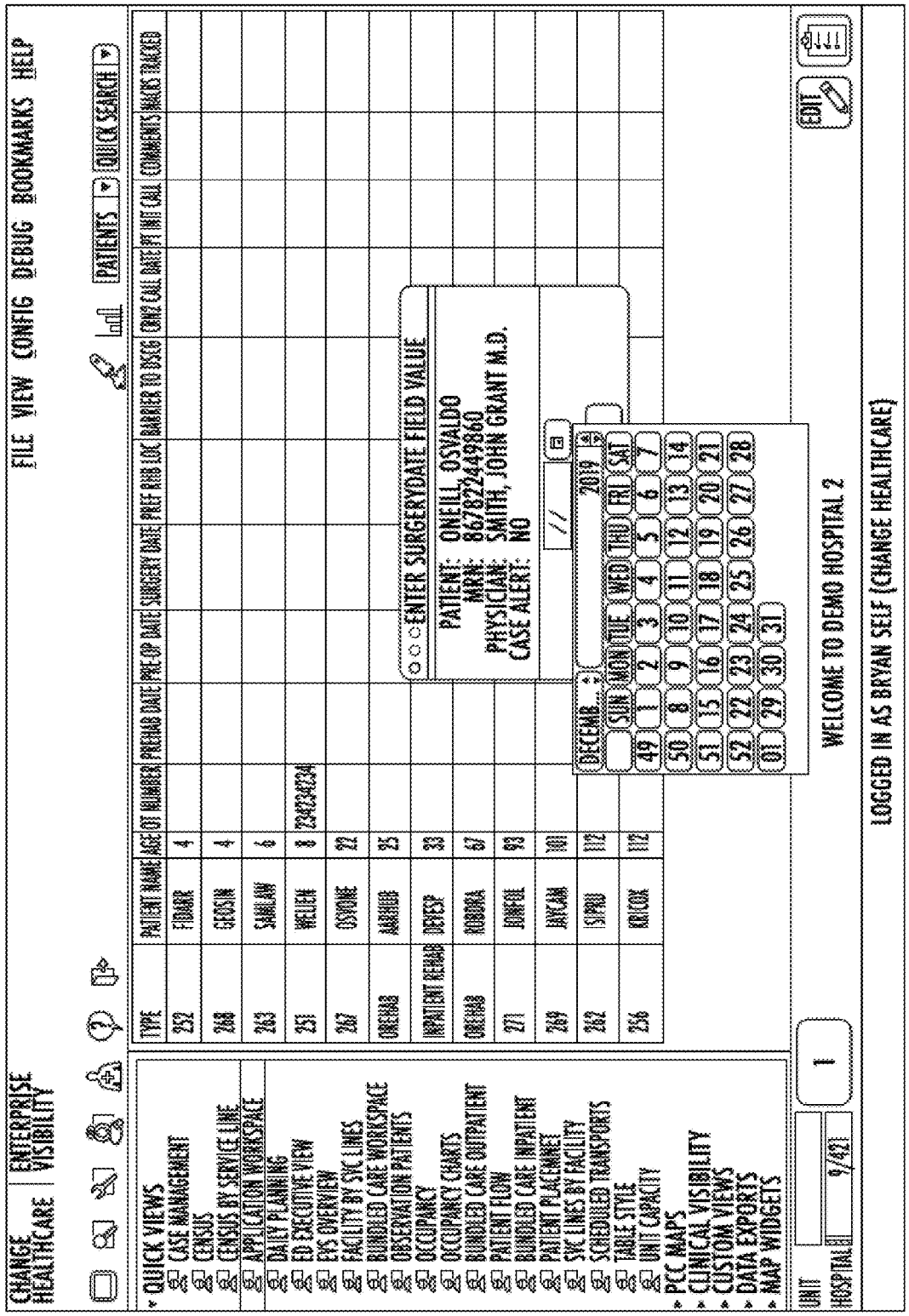

Having thus described embodiments of the invention in general terms, reference will now be made to the accompanying drawings, which are not necessarily drawn to scale, and wherein:

FIG. 1 is an overview of a system that can be used to practice some example embodiments described herein;

FIG. 2 is an exemplary schematic diagram of an apparatus in accordance with some example embodiments;

FIG. 3 is a flowchart of operations that may be performed in accordance with some example embodiments;

FIG. 4 is an exemplary depiction of a plurality of fields and associated attributes in accordance with some example embodiments;

FIG. 5A is an exemplary depiction of a vector graphic image rendered at a client device in accordance with some example embodiments;

FIG. 5B is an exemplary depiction of a vector graphic image rendered at a client device in accordance with some example embodiments; and FIG. 6 is an exemplary depiction of defining a custom field at a user interface rendered at a client device in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described herein to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

System Architecture and Exemplary Apparatus

FIG. 1 is an overview of a system that can be used to practice certain embodiments described herein and should not be considered limiting. As illustrated in FIG. 1, example embodiments may be implemented as or employed in a distributed system. The various depicted components may be configured to communicate over a network 10, such as the Internet, for example, or any other communication interface as described in further detail hereinafter. In general, client device(s) 30 may be configured to communicate with a server 40 and/or database 50. Client device 30 may include any computing device such as a personal computer, laptop, smart phone, tablet, and/or the like, and may be configured to display content in a browser. In some examples, any number of client devices 30 may be configured to communicate with server 40, which may be configured to process requests from the client device 30, provide data and content to the client device 30, and/or the like. The server 40 may be communicatively connected to database 50 which may be configured to store data, content, and/or the like. The client device 30, server 40 and/or database 50 may be configured to perform any of the operations described herein.

The system of FIG. 1 described above is provided merely as an example implementation and it will be appreciated that the example embodiments provided herein may be implemented as or employed by any number of system architectures.

Referring now to FIG. 2, apparatus 200 is a computing device(s) configured for dynamically updating database tables and generating and updating field tracking forms. Apparatus 200 may at least partially or wholly embody any of the network 10, client device 30, server 40, and/or database 50 described above. Apparatus 200 may therefore implement any of the client device 30, server 40, and/or database 50, in accordance with some example embodiments, or may be implemented as a distributed system that includes any of the network 10, client device 30, server 40, and/or database 50.

It should be noted that the components, devices, and elements illustrated in and described with respect to FIG. 2 below may not be mandatory and thus some may be omitted in certain embodiments. For example, FIG. 2 illustrates a user interface 216, as described in more detail below, which may be optional in the server 40 and/or database 50. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as client device 30, server, 40, database 50, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as apparatus 200, memory 214 may store data records such as those pertaining to a patient, electronic health records, and/or the like.

The memory 214 may be configured to buffer input data for processing by the processor 212. Additionally, or alternatively, the memory 214 may be configured to store instructions for execution by the processor 212. In some embodiments, the memory 214 may include one or more databases, such as database 50, that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a joystick, a display, a touch screen display, a microphone, a speaker, and/or other input/output mechanisms. As such, the user interface 216 may, in some example embodiments, provide means for user control of configuring database tables and/or the like. For example, the user interface 216 may be implemented on the client device 30, for us by a system administrator of a service provider, and/or a practitioner at a healthcare facility and/or the like. In some example embodiments in which apparatus 200 is embodied as server 40, database 50, and/or the like, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst client system 102, application entity 104, application interface 106 and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

The network, such as network 10, in which apparatus 200 and/or any of the components described herein may operate (e.g., client device 30, server 40, database 50, or apparatus 200, and/or the like) may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

Overview

Tracking and storing patient data as well as updating stored patient data in view of new developments may be vital to the overall functionality of a respective healthcare facility (e.g., a hospital, doctor's office, specialized health facility, nursing home, and/or the like). For example, data relating to the care of a patient should be regularly tracked and/or updated (e.g., at each patient visit to a healthcare facility) according to changing requirements for a particular practice or medical specialty. The data needing to be tracked may further change based on changes in insurance guidelines and/or government regulations. Such patient data may comprise demographic data associated with a patient's height, weight, age, name, and/or the like. Personal data of a patient may also need to be tracked and/or updated at various instances. Personal data may comprise a patient's address, social security number, driver's license number, and/or the like. Patient data may also comprise data on the relationship between the patient and the particular healthcare facility, such as number of visits per year, specific medical procedures undergone, physicians seen, and/or the like. The patient data may further comprise certain measurements, lab results, and/or other test results that may be pertinent to the patient's electronic health record. Additionally, financial information associated with a patient may be tracked, such as a patient's insurance plan, Medicare/Medicaid information, deductibles, amounts owed to the healthcare facility, and/or the like.

Traditional methods for tracking, storing, and updating patient data may be burdensome to healthcare practitioners (e.g., doctors, nurses, assistants, medical staff) and service providers for a variety of reasons. For example, one may have to access a system and/or database to retrieve patient data, though, all patient data may not be available from one access request. Attempting to access patient data through numerous user interface forms and/or database requests may be burdensome on a network supporting the healthcare facility. In some circumstances, a healthcare practitioner may need to view particular fields of data of a large number of patients together for comparison purposes. As an example, a doctor may desire to view data on all patients who visited the healthcare facility during a particular month with a similar symptom to find a root cause of a virus outbreak.

In another example, a nurse may need to track historical data of patients who suffered a certain injury along with the pain medication they received in order to provide the correct pain medication to a current patient with the same injury, and time may be of the essence. However, traditional methods and systems may be unable to provide the necessary patient data fields together and in a clear or concise format for the healthcare practitioners to process. For example, a practitioner may have to utilize various user interface forms and/or applications to access the relevant data, and piece together the data accordingly. In another example, a practitioner may need to view or analyze multiple tables of data comprising different fields. For example, a nurse tending to a patient room may need to quickly analyze a plurality of information regarding a patient to make a critical decision (e.g., medication allergy data, blood pressure data, and/or the like). Traditional methods of displaying patient data in a patient room (e.g., a markerboard) may be inefficient compared to other potential methods (e.g., a television or monitor displaying multiple fields of patient data).

In some examples, a user may want to track a new field or element that has not yet been tracked for a particular patient or for any patient. Configuring a server and/or database to provide the new field or element may require significant overhead, such as submitting a computer application change request, a software developer or system administrator programming the change, and rebooting or bouncing a software server so that the change is reflected on the client side. Example embodiments may alleviate some or all of the aforementioned problems as provided below.

Example Process for Practicing Embodiments of the Present Disclosure

FIG. 3 is a flowchart illustrating example operations of an apparatus 200 according to some example embodiments. The operations of FIG. 3 may be performed by apparatus 200 to manage the dynamic tracking of data during a client-server session and to dynamically update a database accordingly. In particular, example embodiments provide for managing retrieval of data to be displayed in a table at a client device, such as but not limited to medical data, financial data, calendar data, or any other type of records data. Example embodiments are described with respect to the non-limiting example of tracking one or more fields related to medical data, and more specifically, patient data. However, it will be appreciated that embodiments disclosed herein may be used in a variety of fields and/or practices.

As shown by operation 300, apparatus 200 may include means, such as processor 212, memory 214, communication interface 218, user interface 216 and/or the like, for receiving a request for data associated with at least one record and an application identifier. In an example embodiment, the request may be received at a server, such as server 40, from a client device 30 during a client-server session. The client device 30 may be associated with a healthcare system and may comprise a desktop computer, laptop, tablet, mobile device, or the like. For example, a user, such as a healthcare practitioner, may access a user interface 216 of client device 30 in order to transmit the request to server 40 via a network 10. As another example, a system administrator of a service provider tasked with providing an information management system to a healthcare practice or other organization may access a user interface 216 of client device 30 to initiate a request.

The request received at server 40 may comprise data associated with at least one record and an application identifier. In some embodiments, the application identifier may be preconfigured and associated with a plurality of fields, enabling a user to make a selection of the application identifier (or content associated therewith) at the client device 30 to request to view the plurality of fields for a particular record or subset of records. For example, in some embodiments, the data associated with the at least one record may be associated with a respective patient and may comprise a respective patient identifier. In this regard, the request received at the server 40 may include an application identifier, and one or more patient identifiers. The application identifier may be associated with an application bundle defining the fields to be displayed in the particular application, table, or view, described in further detail below.

As shown by operation 302, apparatus 200 may include means, such as processor 212, memory 214, communication interface 218, and/or the like, for retrieving, from a database table, values associated with a plurality of fields associated with the application identifier and the at least one record. For example, upon receiving the request as detailed above in operation 300, the server 40 may process an application form, such as a JavaServer Page (JSP) associated with the application identifier to retrieve values associated with the plurality of fields associated with the application identifier and the at least one record of the request from database 50. In some embodiments, the server may use a Model-View-Controller (MVC) architecture when processing the application form. In this regard, the server 40 may serve as the controller by storing data necessary for processing the application form, the retrieved values may serve as the model, and the application form may serve as the view. In some embodiments, the application form (e.g., JSP) may reference an application bundle, such as one or more XML files, that defines the plurality of fields. For example, FIG. 4 depicts an exemplary application bundle comprising a plurality of fields associated with an application identifier. Each field may comprise one or more attributes related to the field. For example, the one or more attributes may include identifiers to the server 40 and/or database 50 to identify and/or access data associated with the respective field. The plurality fields are defined in the application bundle such that values of the respective fields can be retrieved for a particular record, or records, such as patients, and included together in a structured document. As an example, each field in FIG. 4 is associated with an application identifier, "BUNDLE A."

The one or more attributes may also comprise a widget type attribute. The widget type attribute may indicate to the server 40 that the respective field is to be associated with a particular widget during generation of a structured document by server 40. In some examples, the widget type attribute may comprise a number value associated with a particular widget type. In an embodiment, a widget type attribute comprising a value of '0' may indicate that the field is to be associated with a checkbox widget. Similarly, in one embodiment, a widget type attribute comprising a value of '1' may indicate that the field is to be associated with a textbox widget, and a value of '2' may indicate that the field is to be associated with a calendar date widget. In this regard, the widget type may be considered a graphical editor type or input type, enabling efficient entry of data for the particular field at a client device 30, as described in further detail below. Additionally, or alternatively, the widget type may dictate the type of field configured in the database for storing the respective data. For example, a column or field of a database may be configured to store integers, dates, text strings, and/or the like.

According to example embodiments, certain fields of patient data associated with the at least one record may be accessed and retrieved from the database 50 by the server 40 based on the data included in the request. As an example, the received request may comprise data associated with two records (e.g., patient identifiers) for Patient A and Patient B. Additionally, the application identifier for viewing scheduled surgeries, may be preconfigured and associated with three fields: patient age, gender, and scheduled surgery date. In this example, the server 40 may access the database 50 in order to retrieve stored values associated with the age, gender, and scheduled surgery date of Patient A and Patient B.

In some embodiments, the received request may further comprise data associated with the user and/or client device that initiated the request. For example, a role identifier may be included in the request and may indicate a particular role of the user within the healthcare system and whether that user is authorized to retrieve values associated with particular patient data fields. Certain aspects of patient data may be classified and only available to select roles (e.g., doctors, nurses, surgeons) and unavailable to other roles (e.g., medical staff, receptionists, or the like). Certain patient data may be classified in accordance with one or more regulatory healthcare standards and/or privacy standards, such as in accordance with the Health Insurance Portability and Accountability Act (HIPAA).

In an embodiment in which the received request comprises data associated with a role identifier, the apparatus 200 (e.g., server 40) may be configured to determine if the one or more fields associated with the request are authorized to be accessed based on the role identifier associated with the request. For example, patient health information (PHI) access rights may be stored on database 50 in association with one or more role identifiers. The server 40 may access the database 50 to retrieve data associated with PHI access rights of a particular role identifier that is associated with the request. In this regard, in an instance in which the determination is made that the one or more fields are not authorized to be accessed by the user associated with the role identifier, the apparatus 200 (e.g., server 40) may transmit an indication of a denial of the request to the client device 30.

In an instance in which the determination is made by the server 40 that the one or more fields are authorized to be accessed based on the role identifier, the server 40 may proceed to retrieve values associated with a plurality of fields associated with the application identifier and the at least one record of the request.

At operation 304, apparatus 200 may include means, such as processor 212, memory 214, communication interface 218, and/or the like, for generating a structured document comprising the plurality of fields and the retrieved respective values. For example, after retrieving the respective values (e.g., patient data) associated with the plurality of fields of the request from the database 50, the server 40 may generate a structured document comprising data associated with the plurality of fields and the retrieved respective values. In some embodiments, the structured document may be generated based on one or more commands in the application form, such as the JSP. In this regard, the server may process stored computer code instructions, such as a JSP, in order to generate a structured document and to incorporate therein the values retrieved from the database 50 with respect to operation 302. In some embodiments, the structured document generated by the application form may comprise an XML-based document, such as a Scalable Vector Graphics (SVG) document. In this regard, the structured document may comprise computer-readable instructions to be utilized by the client device 30 to render a vector graphic image, such as a form or table. The structured document, such as the SVG document may comprise the plurality of fields, and retrieved respective values, such as patient data, and formatting information. The vector graphic image may cause display the data in as tabular format for display as is illustrated in FIG. 5A.

At operation 306, apparatus 200 may include means, such as processor 212, memory 214, communication interface 218, and/or the like, for embedding, in the structured document, a script enabling customization of the structured document. For example, the script may comprise computer program instructions, such as one or more ECMAScript commands for enabling customization of the structured document at the client device 30. For example, as described in further detail below, the embedded script may allow a user, while viewing a form (e.g., vector graphic image) rendered by the client device 30 according to the structured document, to perform customization of the form. Such customization is described in further detail below and may include but is not limited to selecting and/or highlighting one or more cells, sorting one or more rows and/or columns of the structured document, inserting new data into one or more cells of the form, and/or the like.

At operation 308, the apparatus 200 may include means, such as processor 212, memory 214, communication interface 218, and/or the like, for transmitting the structured document and the embedded script to the client device 30. In this regard, as the server 40 has configured the structured document to generate a vector graphic image, the client device 30 may process the structured document, and transform data therein into a human-readable vector graphic image via a rendering application, such as but not limited to Apache Batik. It is to be appreciated that other types of rendering applications may be employed to produce a table or other readable interface. In any event, the structured document generates a vector graphic image and the vector graphic image may be rendered for display (e.g., via user interface 216) at the client device 30.

An example vector graphic image generated from a structured document and rendered at a client device 30 is provided in FIG. 5A. As depicted, the vector graphic image comprises data in a tabular form, with each column representing a respective field (such as Patient Name, Age, Prehab Date, Surgery Date, etc.) and each row representing a respective patient. Cells of the table comprise the values retrieved from the database 50. The vector graphic image and embedded script may enable user customization at the client device 30, as described in further detail below.

At operation 310, the apparatus 200 may include means, such as processor 212, memory 214, communication interface 218, and/or the like, for receiving an indication of at least one custom field and values of the at least one custom field. As introduced above, the script (e.g., computer program code such as ECMAScript) embedded in the structured document, enables a user to interact with the vector graphic image (e.g., form) at client device 30 in a variety of ways, including but not limited to entry of a custom field, and values thereof pertaining to a particular record.

For example, a user may select a cell of the table of the vector graphic image in order to add or update new information for a particular field associated with a patient. As an example, in the table depicted in FIGS. 5A and 5B, a user may select cell 505 in order to update a surgery date of a particular patient. In this regard, based on user selection of the cell, example embodiments may enable entry via a graphical editor or widget type defined by the associated application bundle. The script may receive the information input by the user via the associated widget or graphical editor and transmit the updates to the server 40 for updating at the database 50 accordingly.

As another example of user customization by interaction with the displayed form (e.g., vector graphic image), and as indicated by operation 310, a user may provide new, custom fields (e.g. columns) at the client device during the client-server session.

The user may then enter values of the new or custom fields in association with the at least one record. The term "custom field" is used herein to indicate that the field or column does not exist in the database 50 at the time of customization or entry by the user at the client device 30, but that the user interacts with the displayed form to cause the creation of the custom field in the database 50 as described below. In this regard, a user may interact with the form, such as by right-clicking, and providing free form text to enter a name of a custom field. The customer field and/or name thereof provided by the user may be any arbitrary data point a user wishes to track. As shown in FIG. 6, the form may further display a dropdown menu or other selectable indication of widget types so that a user may select the widget type to be associated with the custom field. For example, the user may select from a calendar and date widget type, numeric widget type, text widget type, and/or the like. It will be appreciated that other methods of user input may be utilized to interact with the form to add a custom field and to configure the custom field to be restricted to certain input types or other data constraints.

At operation 312, the apparatus 200 may include means, such as processor 212, memory 214, communication interface 218, and/or the like, for adding, during the client-server session, the at least one custom field to the database table and storing the values of the at least one custom field. In certain embodiments, the new custom field added to the database may be configured with constraints reflecting the widget type selected by the user. For example, a new custom field may be limited to numeric values, text values, dates, and/or the like. In certain embodiments, the values of the at least one custom field are stored in association with a respective record (e.g., patient).

It will be appreciated that according to certain embodiments, once the custom field is added in the database 50 by the server 40, the server 40 may update the structured document as to include the updated values of the at least one custom field. According to certain embodiments, the structured document may then be transmitted to the client device 30 and re-rendered for display at the client device 30 comprising the newly added field. Due to the implementation of the structured document and embedded script, and the real-time updates at the server responsive to the addition of new fields, the updating of the document at the client device 40 may be performed seamlessly, providing "on the fly" or real-time customization during the client-server session.

Example embodiments therefore enable the custom fields to be added to the database 50, along with respective values provided by the user, and to be reflected in the form displayed at the client device 30, in real-time or near real-time responsive to the user provision of the custom fields at the client device 30 during the client-server session. The application bundles, which may be formatted in XML or another structured language, may therefore also be updated on the server 40 in real-time or near real-time during the client-server session. Additionally, or alternatively, if a new application is created on the client device 30 using the form generated by the server 40, a new application bundle may be generated on the server 40 in real-time or near real-time during the client-server session.

Example embodiments therefore enable users of the client device 30, such as healthcare practitioners and/or other users to add new fields to the database 50 and to configure custom views of desired fields, without necessarily requiring special requests, development work at the server 40 and/or database 50, or rebooting or bouncing of the server 40. In this way, a server managing the data (e.g., server 40) need not reboot in order to provide desired data to a client device, and to enable user configuration at the client device. Additionally, providing data values associated with numerous patient identifiers allows for a succinct view of data within a customizable vector graphics image for efficient comparison and analysis purposes.

As described above, example embodiments enable real-time generation or modification of application bundles at the server 40, such as in an XML format, to define groupings of fields for display in a form at the client device 30. In this regard, the user customization at the client device 30 may result in modified or new applications bundles being stored on the server 40.

Accordingly, at operation 314, apparatus 200 may include means, such as processor 212, memory 214, communication interface 218, and/or the like, for exporting the application bundle from a first region to at least a second region to cause the at least one custom field to be added to at least a second database table of the second region. According to example embodiments, the modified or new applications bundles may then be exported to, copied to, or cloned in different regions or environments such that the customizations may be utilized by other organizations, user groups, and/or the like.

For example, an administrator or other user may utilize a user interface 216 via a client device 30, to configure desired custom fields according to example embodiments discussed herein. The configuration may be performed in a test region, test environment, or for a region of the server 40 and/or database 50 designated for a particular customer or organization, such as but not limited to a particular healthcare provider or practice. Once optionally tested, the modified or newly generated application bundles (e.g., XML) may be deployed in another region or environment so that forms corresponding to the application bundles may be accessed and used in the other region or environment. Accordingly, the database in the other region or environment may be updated to reflect the data in the application bundle. In this regard, an application bundle generated based on customization by a system administrator in a test region may be deployed for use by all customers or organizations or any number of customers or organizations, such as via their respective client device 30. As another example, a customer or organization, such as one healthcare provider or practice, may customize an application bundle, which may be exported for use by another customer or customers.

It will be further appreciated that example embodiments of the present disclosure may enable a user to manually configure or create an application bundle (e.g., XML) to be deployed in an environment, thereby resulting in the creation of the associated fields in a database and access by a user via the client device 30. In this regard, a user such as a system administrator given particular access rights may copy or clone an application bundle and make changes to the underlying computer program code such as XML to configure custom fields.

Example embodiments may be further configured to integrate with Health Level 7 (HL7) interfaces. In some embodiments, the apparatus 200 may include means, such as processor 212, memory 214, communication interface 218, and/or the like, for receiving a file from a (HL7) server. In this regard, the file may comprise data formatted in accordance with HL7. In an instance in which an HL7 file comprising patient data is received at the server 40, the server 40 may auto-populate data from the file into the database table stored in database 50. For example, one or more fields of data may need to be updated based on the HL7 file. The server 40 may be configured to determine one or more values associated with the one or more fields of data and extract the one or more values from the HL7 file associated with one or more fields to be dynamically updated in the database table upon receiving the HL7 file at the server 40. In some embodiments, the server 40 may be configured to convert the HL7 file into an XML file prior to extracting the one or more values. In this regard, the XML file may be processed by the server 40 in order to extract the one or more values to be updated. Accordingly, custom fields added to the database 50 that are already utilized by an HL7 protocol may be auto-populated according to a received HL7 file. In this regard an application bundle may be configured, such as by a system administrator, to include fields that match or are associated with fields provided by an HL7 interface as may be defined in an HL7 data specification.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagram, and combinations of operations in the flowchart or diagram, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   receiving at a server, from a client device during a client-server session, a request for data associated with at least one record and an application identifier;
   processing an application form associated with the application identifier to: (a) retrieve, from a first database table in a first region, values associated with a plurality of fields associated with the application identifier and the at least one record, and (b) generate a structured document comprising the plurality of fields and the retrieved respective values;
   embedding, in the structured document, a script enabling customization of the structured document;
   transmitting the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server;
   receiving, at the server, the indication of the at least one custom field and the values of the at least one custom field;
   during the client-server session, adding the at least one custom field to the first database table and storing the values of the at least one custom field; and
   exporting the application bundle to at least a second region to cause the at least one custom field to be added to at least a second database table of the second region.

2. The method of claim 1, wherein processing the application form further comprises accessing an application bundle comprising Extensible Markup Language (XML) and defining the plurality of fields associated with the application identifier; and wherein the method further comprises:
   during the client-server session, modifying the application bundle or generating a new application bundle comprising XML and reflecting the at least one custom field.

3. The method of claim 1, wherein the script is further configured to, when executed by the client device, receive an indication of at least one respective widget type to be associated with the at least one custom field.

4. The method of claim 1, wherein the at least one record is associated with at least one patient identifier.

5. The method of claim 1, wherein processing the application form, embedding the script, and transmitting the structured document are performed in real-time or near real-time.

6. The method of claim 1, wherein the script comprises one or more ECMAScript commands.

7. The method of claim 1, wherein the structured document is a Scalable Vector Graphics (SVG) document.

8. The method of claim 1, wherein the structured document is dynamically generated using JavaServer Pages (JSP).

9. The method of claim 1, wherein the request comprises a role identifier, and the method further comprises:
   determining whether a user associated with the role identifier is authorized to access the plurality of fields; and
   in an instance in which the user is not authorized to access the plurality of fields, transmitting an indication of a denial of the request to the client device.

10. The method of claim 1, wherein the displayed structured document is updated in real-time or near real-time to reflect the at least one custom field and the respective entered values.

11. The method of claim 1, further comprising:
    receiving a file from a Health Level 7 server; and
    auto-populating data from the file into the database table.

12. An apparatus comprising at least one processor and at least on memory including computer program code, the at least one memory and the computer program code configured to, with the processor, cause the apparatus to at least:
    receive, from a client device during a client-server session, a request for data associated with at least one record and an application identifier;
    process an application form associated with the application identifier to: (a) retrieve, from a first database table in a first region, values associated with a plurality of fields associated with the application identifier and the at least one record, and (b) generate a structured document comprising the plurality of fields and the retrieved respective values;
    embed, in the structured document, a script enabling customization of the structured document;
    transmit the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server;
    receive, at the server, the indication of the at least one custom field and the values of the at least one custom field;
    during the client-server session, add the at least one custom field to the database table and store the values of the at least one custom field; and
    export the application bundle to at least a second region to cause the at least one custom field to be added to at least a second database table of the second region.

13. The apparatus of claim 12, wherein processing the application form further comprises accessing an application bundle comprising Extensible Markup Language (XML) defining the plurality of fields associated with the application identifier;
    and wherein the apparatus is further configured, with the at least one memory and the computer program code, to:
        during the client-server session, modifying the application bundle or generating a new application bundle comprising XML and reflecting the at least one custom field.

14. The apparatus of claim 12, wherein the script is further configured to, when executed by the client device, receive an indication of at least one respective widget type to be associated with the at least one custom field.

15. The apparatus of claim 12, wherein the at least one record is associated with at least one patient identifier.

16. The apparatus of claim 12, wherein processing the application form, embedding the script, and transmitting the structured document are performed in real-time or near real-time.

17. The apparatus of claim 12, wherein the displayed structured document is updated in real-time or near real-time to reflect the at least one custom field and the respective entered values.

18. A computer program product comprising at least one non-transitory computer-readable storage medium having computer-executable program code instructions stored therein, the computer-executable program code instructions comprising program code instructions to:
    receive, from a client device during a client-server session, a request for data associated with at least one record and an application identifier;
    process an application form associated with the application identifier to: (a) retrieve, from a first database table in a first region, values associated with a plurality of fields associated with the application identifier and the at least one record, and (b) generate a structured document comprising the plurality of fields and the retrieved respective values;
    embed, in the structured document, a script enabling customization of the structured document;
    transmit the structured document and the embedded script to the client device, wherein the structured document, when processed by the client device, generates a vector graphic image configured for rendering, at the client device, the retrieved values of the plurality of fields for the at least one record, and wherein the script is configured to, when executed by the client device: (a) receive an indication of at least one custom field provided at the client device during the client-server session, (b) receive entered values of the at least one custom field in association with the at least one record, and (c) transmit the indication of the at least one custom field and the respective entered values in association with the application identifier and the at least one record to the server;
    receive, at the server, the indication of the at least one custom field and the values of the at least one custom field;
    during the client-server session, add the at least one custom field to the database table and store the values of the at least one custom field; and
    export the application bundle to at least a second region to cause the at least one custom field to be added to at least a second database table of the second region.

* * * * *